United States Patent [19]
Chasak et al.

[11] Patent Number: 6,090,138
[45] Date of Patent: *Jul. 18, 2000

[54] UNIVERSAL HEART VALVE HOLDER

[75] Inventors: Frank Edward Chasak, Austin; Paul E. Whiting, Pflugerville, both of Tex.

[73] Assignee: Sulzer Carbomedics Inc., Austin, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 09/012,498

[22] Filed: Jan. 23, 1998

[51] Int. Cl.$^7$ .......................................................... A61F 2/24
[52] U.S. Cl. ................................................................ 623/2
[58] Field of Search ........................... 623/2, 900; 606/1, 606/99; 206/438, 525

[56] References Cited

U.S. PATENT DOCUMENTS

| | | | |
|---|---|---|---|
| 3,860,005 | 1/1975 | Anderson, et al. ...................... | 128/303 |
| 4,585,453 | 4/1986 | Martin, et al. ............................... | 623/2 |
| 4,655,218 | 4/1987 | Kulik, et al. ............................. | 128/321 |
| 4,679,556 | 7/1987 | Lubock, et al. ......................... | 128/303 |
| 4,683,883 | 8/1987 | Martin ...................................... | 128/303 |
| 4,801,015 | 1/1989 | Lubock et al. ........................... | 206/438 |
| 4,865,600 | 9/1989 | Carpentier et al. .......................... | 623/2 |
| 5,236,450 | 8/1993 | Scott .......................................... | 623/2 |
| 5,350,420 | 9/1994 | Cosgrove, et al .......................... | 623/2 |
| 5,360,014 | 11/1994 | Sauter, et al. ........................... | 128/774 |
| 5,403,305 | 4/1995 | Sauter, et al. .............................. | 606/1 |
| 5,443,502 | 8/1995 | Caudillo et al. ............................ | 623/2 |
| 5,480,425 | 1/1996 | Ogilive ...................................... | 623/2 |
| 5,531,785 | 7/1996 | Love, et al. ................................. | 623/2 |
| 5,571,215 | 11/1996 | Sterman, et al. .......................... | 623/66 |
| 5,578,076 | 11/1996 | Krueger, et al. ............................. | 623/2 |
| 5,582,607 | 12/1996 | Lackman .................................... | 606/1 |
| 5,713,951 | 2/1998 | Garrison, et al. ........................... | 623/2 |
| 5,713,952 | 2/1998 | Vanney, et al. ............................. | 623/2 |
| 5,876,437 | 3/1999 | Vanney, et al. ............................. | 623/2 |

FOREIGN PATENT DOCUMENTS

WO 92/12688  6/1992  WIPO .

*Primary Examiner*—George Manuel
*Attorney, Agent, or Firm*—Timothy L. Scott; Philip S. Lyren; Kenneth S. Barrow

[57] ABSTRACT

A prosthetic heart valve holder includes a valve holder selectively attachable with a handle assembly. The handle assembly includes a handle end, a flexible, medial segment, and a coupling member. The valve holder includes a valve coupling member and a handle receiving member. The valve coupling member may include a leaflet bias member, leaflet guards, or both. The handle receiving member includes locking tabs and receiving windows for receiving the handle coupling member. The handle receiving member also includes anti-rotation stays which serve to transfer rotational forces from the handle assembly to the valve holder. Also, alignment stays serve to properly align the handle receiving member with the coupling member so that the handle assembly and valve holder are properly coupled. The handle assembly is made from resterilizable materials so that the handle assembly may be reused. The valve holder is disposable.

14 Claims, 2 Drawing Sheets

UNIVERSAL HEART VALVE HOLDER

SUMMARY OF THE INVENTION

The invention relates to prosthetic heart valves, namely, an apparatus for holding a prosthetic heart valve during implantation of the valve.

Prosthetic heart valves are used to replace native heart valves that are damaged or otherwise unable to properly regulate blood flow through the heart. Typically, the native valve is excised from the heart and a prosthetic valve is attached to the native valve annulus. There are two general types of prosthetic valves, mechanical valves and bioprosthetic valves. A mechanical valve includes an annular ring which supports one or more leaflets.

When using a mechanical valve, a sewing ring is positioned circumferentially around the outer surface of the annular ring. The sewing ring is sutured to the native annulus and, over time, native tissue grows onto the sewing ring and annular ring to provide a secure attachment. When attaching a mechanical valve, a surgeon does not directly handle the valve, thereby maintaining the sterility of the valve and avoiding any possible damage to the valve. Typically, a valve holder is pre-attached to a valve, either during the packaging of the valve or prior to an implantation procedure.

The valve holder should allow the surgeon to position the valve (and sewing ring) in the native annulus, this includes both axial and rotational movement of the valve. Therefore, the valve holder should be able to withstand the axial and rotational loads required to properly position the valve. The valve holder should also occupy minimal space to allow the surgeon good visual access of the implantation area. Also, the valve holder should be easy to use. Finally, the valve holder should be low cost.

SUMMARY OF THE INVENTION

According to the present invention, a two-part prosthetic heart valve holder is provided. The first valve holder portion includes a heart valve coupling member that is operably connected with a handle receiving member. This first portion is disposable. The second portion is the handle assembly. The handle assembly is reusable.

The handle receiving member includes an annular receiving neck, generally opposed locking tabs positioned on an inner surface of the receiving neck, generally opposed interior walls on the receiving neck defining receiving windows, generally opposed anti-rotation stays spaced axially from the receiving windows, and a plurality of alignment stays spaced axially from the receiving windows. Consequently, axial and rotational forces from the handle assembly are transferred to the first portion of the valve holder. Further, the handle assembly and valve holder are securely locked together. The dimensions of the neck and related structures control the locking force between the handle assembly and valve holder, as well as define any play between the two parts. Also, the alignment stays provide easy alignment between the handle assembly and valve holder.

The handle receiving member includes a suture groove in an outer surface of the receiving neck extending generally orthogonal to the longitudinal axis of the receiving neck, a suture cutting groove in the outer surface of the receiving neck positioned orthogonal to and intersecting with the suture groove, and opposed cutting guides positioned adjacent the cutting groove. This configuration, in combination with the suture eyelets disclosed below, allows a single suture to be threaded through the valve sewing ring and valve holder, thereby coupling the sewing ring with the heart valve and holder, and allowing a surgeon to position the entire assembly as desired. In order to remove the valve holder, a surgeon need cut only one suture, and the cutting groove and guides provide an easy configuration for the surgeon to find the suture and cut it without fear of damaging the valve or heart tissue.

The heart valve coupling member includes an annular disk and a cross member extending from one side of the disk to a generally opposite side, providing rigidity to the disk. Also, the heart valve coupling member may include a leaflet bias member and/or generally opposed leaflet guards extending axially from the disk.

The handle assembly is selectively attachable with the handle receiving member. The handle assembly includes a handle end, a medial segment, and a coupling assembly. The coupling assembly includes a generally annular body, generally opposed locking rings extending radially outward from the annular body, generally opposed anti-rotation grooves extending between the locking rings, and a plurality of alignment grooves extending axially along the locking rings.

DETAILED DESCRIPTION OF THE EMBODIMENTS

Figure 1:
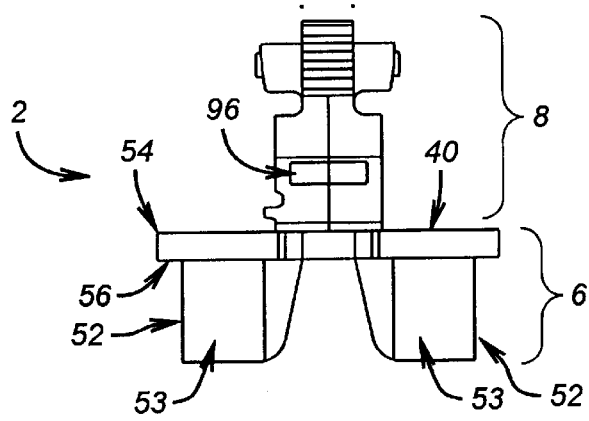
FIG. 1 is a side view of a heart valve holder and handle assembly.

As shown in FIG. 1, a heart valve holder 2 is selectively coupled with a handle assembly 4. Valve holder 2 includes a valve coupling member 6 and a handle receiving member 8. Handle assembly 4 includes a grasping end 10, a medial segment 12, and a coupling assembly 14.

Handle assembly 4 is made from biocompatible, repeatedly sterilizable materials; preferrably, grasping end 10 and coupling assembly 14 are made from polysulfone and medial segment 12 is made of 316 or 302 stainless steel. Grasping end 10 includes a ribbed or textured outer surface 11. Also, grasping end 10 may be tapered or otherwise formed to provide a more ergonomic grasping area. Medial segment 12 is generally annular in cross section and made from flexible materials which allow a surgeon to bend grasping end 10 relative to coupling assembly 14 during implantation. Consequently, the surgeon has greater flexibility in positioning a valve while obtaining a desired view of the implantation area.

Figure 2:
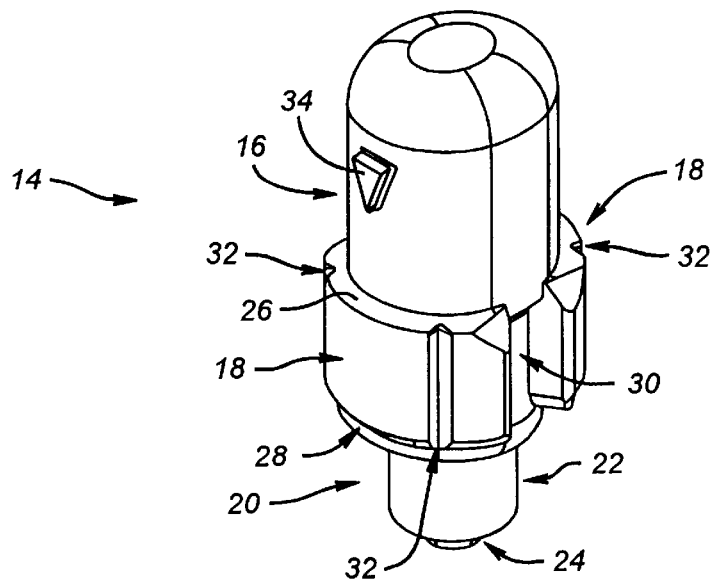
FIG. 2 is a three quarters view of a coupling assembly of a handle assembly.

As shown in FIG. 2, coupling assembly 14 includes a generally annular body 16. Two locking rings 18 are positioned toward the proximal end 20 of coupling assembly 14. An annular guide shaft 22 extends to proximal end 20, and includes engaging surface 24. Locking rings 18 are disposed generally symmetrically about coupling member 14 and extend radially outward from body 16, thereby defining locking lip 26 and tapered engaging surface 28. The outer surfaces of annular body 16 which extend axially between locking rings 18 define anti-rotation grooves 30 (only one groove 30 is shown in FIG. 2). Additionally, alignment grooves 32 extend axially along locking rings 18. In the embodiment shown in FIG. 2, there are four alignment grooves 32, spaced about ninety degrees apart (only three grooves 32 are shown in FIG. 2). One or more alignment indicators 34 are positioned on annular body 16.

Figure 3:
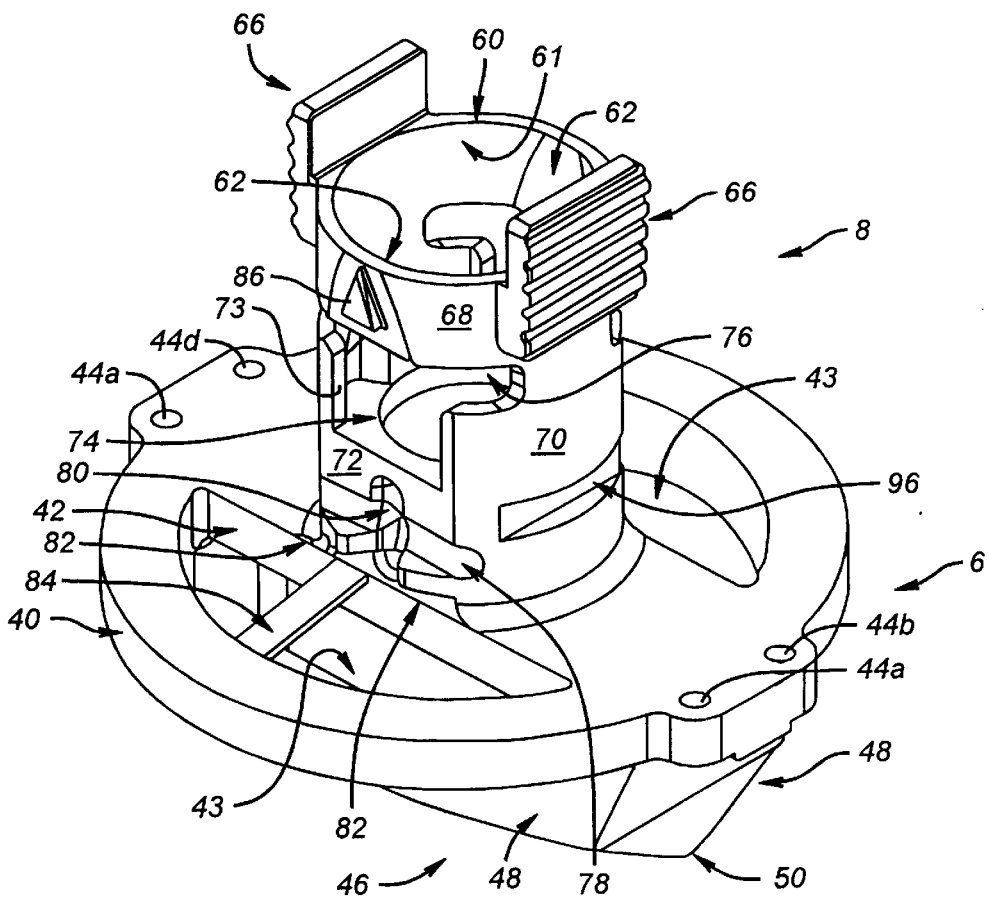
FIG. 3 is a three quarters view of a heart valve holder.

Valve holder 2 is shown in FIG. 3. Valve holder 2 is made from polyetherimide and is disposable, whereas handle assembly 4 may be re-sterilized and reused. Valve coupling member 6 includes annular disk 40. Cross member 42 extends across disk 40, providing rigidity to disk 40 and supporting handle receiving member 8. The voids between disk 40 and cross member 42 define viewing windows 43, which allow a surgeon to view the heart valve and native valve annulus during the implantation procedure. Suture eyelets 44a–d are formed in the radially outward extent of cross member 42.

Leaflet bias member 46 extends axially from disk 40, opposite handle receiving member 8. Leaflet bias member 46 includes generally opposed surfaces 48 which taper toward each other, joining as bias surface 50. When valve holder 2 is coupled with a aortic valve, the valves should be closed during implantation. Leaflet bias member 46 bias the aortic valve leaflets closed without placing undue stress on the leaflets.

In another embodiment shown in FIG. 1, leaflet guards 52 extend axially from disk 40. Leaflet guards 52 include generally arcuate outer surfaces 53 which conform to the inner surface of a valve ring, thereby supporting the valve and protecting the valve leaflets. Leaflet guards 52 are positioned radially inward from the outer edge 54 of disk 40, defining flange 56. Flange 56 provides a limiting surface when valve holder 2 is coupled with a heart valve. In another embodiment, valve coupling member 6 includes leaflet bias member 46 and leaflet guards 52.

Referring again to FIG. 3, handle receiving member 8 includes a generally annular receiving neck 60. The inner surface 61 of neck 60 includes two opposed surfaces 62 which are generally tapered radially inward, defining locking tabs. Two finger pads 66 are positioned on the outer surface 68 of neck 60 and are spaced about ninety degrees from locking tabs 62. Finger pads 66 may include a ribbed or textured surface to provide a more secure contact surface.

Receiving neck 60 extends axially toward cross member 42. The cross sectional shape of neck 60 changes to semi-arcuate beyond locking tabs 62. Two generally arcuate walls 70 are positioned opposite each other and are connected by two generally parallel walls 72 (only one each of walls 70 and 72 are shown in FIG. 3). An inner wall 73 on each wall 72 defines a generally "T" shaped void which function as locking ring receiving windows 74. The upper, horizontal portion 76 of windows 74 serves as a flexure relief areas for neck 60.

A suture groove 78 extends along one of walls 72 adjacent cross member 42. A suture cutting groove 80 is positioned in a medial portion of suture groove 78 and extends generally perpendicular to groove 78. Suture cutting guides 82 are spaced laterally from suture cutting groove 80. Suture cutting stop 84 extends from cross member 42 to disk 40 adjacent suture cutting groove 80. Alignment indicator 86 is positioned on neck 60.

Figure 4:
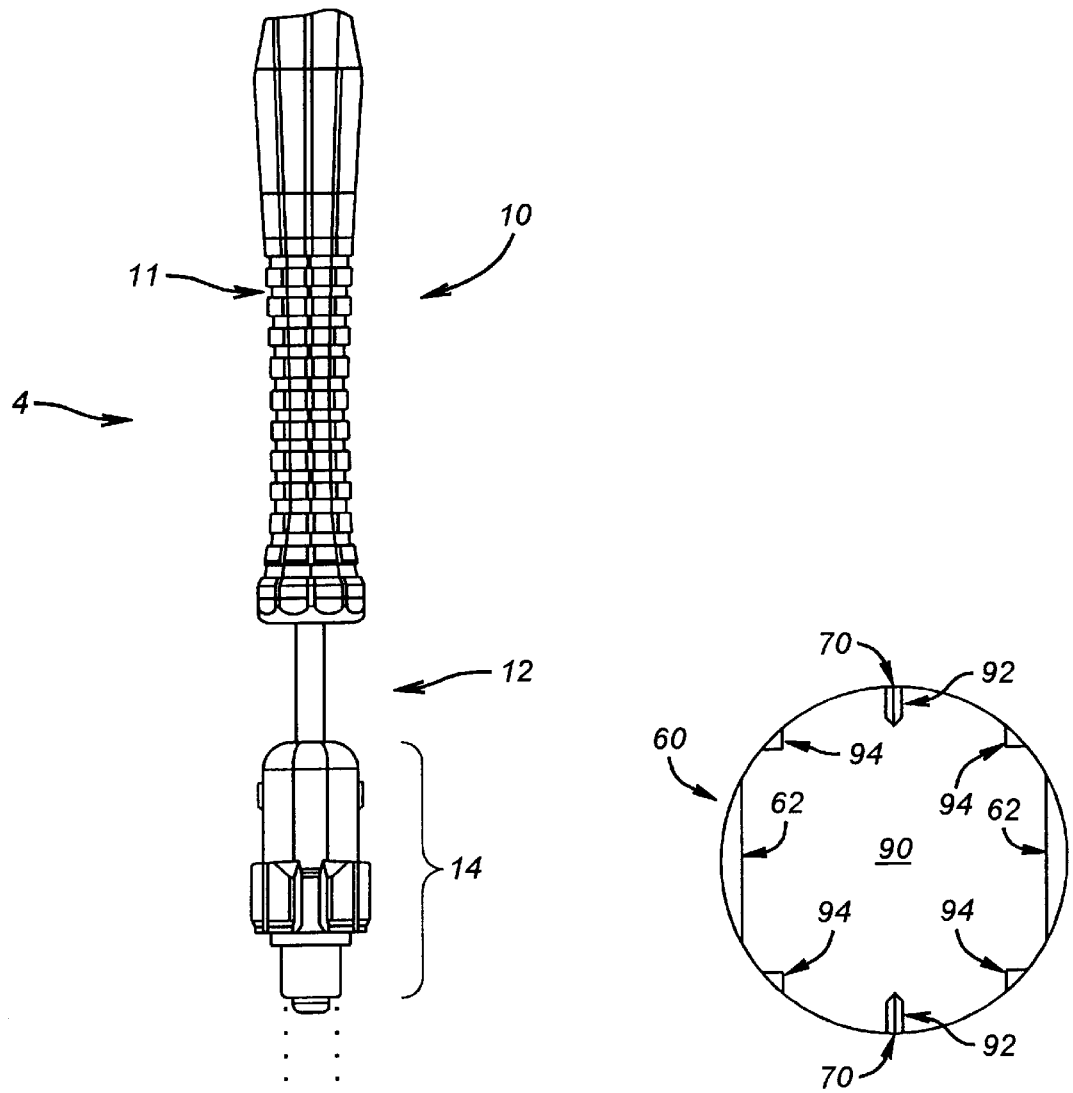
FIG. 4 is an axial view of a heart valve holder.

As shown in FIG. 4, neck 60 extends to a receiving surface 90. Extending axially from receiving surface 90 are anti-rotation stays 92, positioned generally opposite each other along the inner surface of walls 70. Additionally, alignment stays 94 extend axially from receiving surface 90 and are positioned generally ninety degrees apart. The upper extent of stays 92 and 94 are tapered.

In order to connect handle assembly 4 with holder 2, coupling assembly 14 is extended into neck 60, with engaging surface 24 as the leading portion. Coupling assembly 14 is aligned relative to handle receiving member 8 by aligning alignment indicators 34 and 86. This alignment of indicators 34 and 86 also aligns grooves 32 with stays 94. Consequently, handle assembly 14 and holder 2 may be easily coupled in the appropriate relationship to each other.

As coupling assembly 14 extends into neck 60, locking rings 18 make frictional contact with locking tabs 62. Tapered engaging surface 28 forces locking tabs 62 to flex, allowing locking rings 18 to move past locking tabs 62 and into locking ring receiving windows 74. Locking lip 26 extends radially outward from tabs 62, thereby defining a locked coupling between coupling assembly 14 and handle receiving member 8. As engaging surface 24 extends toward receiving surface 90 and alignment tabs 34 and 86 are aligned, anti-rotation grooves 30 are aligned with anti-rotation stays 92. This alignment of grooves and stays serves to transfer rotational forces from handle assembly 14 to holder 2. Also, the mating of surfaces 24 and 90 serves to transfer axial forces from handle assembly 14 to holder 2.

When using a sewing ring, a suture is strung from a first eyelet 44a into the sewing ring, back out of the sewing ring and into eyelet 44b. Next the suture is strung through groove 78, into eyelet 44c, through the sewing ring and back out through eyelet 44d, where the suture can be knotted. Consequently, the sewing ring is fixed to holder 2 and its associated heart valve by one suture. If the surgeon wants to decouple the sewing ring and holder 2, the surgeon cuts the suture at groove 80. Cutting guides 82 keep the cutting instrument properly positioned and Cutting stop 84 prevents the surgeon from cutting into the heart valve or native valve tissue.

The mating of tabs 62 and lip 26 provides a secure coupling between handle assembly 14 and holder 2. Also, as described above, the axial and rotational forces are transferred from the handle assembly 14 to holder 2. When a surgeon wants to detach holder 2 from handle assembly 14, the surgeon compresses finger pads 66, allowing lip 26 to pass along tabs 62, thereby releasing the lock and allowing coupling assembly 14 to be removed from neck 60.

In another embodiment, coupling assembly 14 includes two generally opposed legs which may be flexed toward each other, in a motion similar to tweezers. The legs provide a snap fit with handle receiving member 8.

Additionally, suspension grooves 96 may be cut in the outer surface of walls 70. Suspension grooves 96 provide slots for receiving suspension arms so that valve holder 2, coupled with a heart valve, may be suspended in jar-like packaging. This packaging configuration effective prevents any contact with the heart valve during storage.

Other embodiments are within the scope of the following claims.

We claim the following:

1. A prosthetic heart valve holder, comprising:
    a heart valve coupling member operably connected with a handle receiving member, wherein the handle receiving member comprises an annular receiving neck, generally opposed locking tabs positioned on an inner surface of the receiving neck, generally opposed interior walls on the receiving neck defining receiving windows, generally opposed anti-rotation stays spaced axially from the receiving windows, and a plurality of alignment stays spaced axially from the receiving windows.

2. The heart valve holder of claim 1, wherein the handle receiving member further comprises a suture groove in an outer surface of the receiving neck extending generally orthogonal to the longitudinal axis of the receiving neck, a suture cutting groove in the outer surface of the receiving neck positioned orthogonal to and intersecting with the suture groove, and opposed cutting guides positioned adjacent the cutting groove.

3. The heart valve holder of claim 1, further comprising generally opposed suspension grooves in an outer surface of the receiving neck.

4. The heart valve holder of claim 1, further comprising generally opposed finger pads coupled with an outer surface of the receiving neck and circumferentially spaced from the locking tabs.

5. The heart valve holder of claim 1, further comprising a handle alignment indicator positioned on an outer surface of the receiving neck.

6. The heart valve holder of claim 1, wherein the heart valve coupling member comprises an annular disk and a cross member extending from one side of the disk to a generally opposite side.

7. The heart valve holder of claim 6, further comprising a plurality of suture eyelets positioned on the cross member.

8. The heart valve holder of claim 6, wherein the heart valve coupling member further comprises a leaflet bias member.

9. The heart valve holder of claim 6, wherein the heart valve coupling member further comprises generally opposed leaflet guards.

10. The heart valve holder of claim 1, further comprising a handle assembly selectively attachable with the handle receiving member.

11. The heart valve holder of claim 10, wherein the handle assembly is made from materials that are repeatedly sterilizable.

12. The heart valve holder of claim 10, wherein the handle assembly comprises a handle end, a medial segment, and a coupling assembly.

13. The heart valve holder of claim 12, wherein the coupling assembly comprises a generally annular body, generally opposed locking rings extending radially outward from the annular body, generally opposed anti-rotation grooves extending between the locking rings, and a plurality of alignment grooves extending axially along the locking rings.

14. The heart valve holder of claim 13, further comprising an alignment indicatorpositioned on an outer surface of the annular body.

* * * * *